(12) United States Patent
Akiyama et al.

(10) Patent No.: US 12,085,542 B2
(45) Date of Patent: Sep. 10, 2024

(54) METHOD FOR MEASURING STOOL CONSISTENCY AND METHOD FOR EVALUATING STOOL STATE USING SAME

(71) Applicant: KABUSHIKI KAISHA YAKULT HONSHA, Tokyo (JP)

(72) Inventors: Takuya Akiyama, Tokyo (JP); Kazunori Matsuda, Tokyo (JP); Junji Fujimoto, Tokyo (JP)

(73) Assignee: KABUSHIKI KAISHA YAKULT HONSHA, Tokyo (JP)

( * ) Notice: Subject to any disclaimer, the term of this patent is extended or adjusted under 35 U.S.C. 154(b) by 457 days.

(21) Appl. No.: 17/413,256

(22) PCT Filed: Dec. 4, 2019

(86) PCT No.: PCT/JP2019/047360
§ 371 (c)(1),
(2) Date: Jun. 11, 2021

(87) PCT Pub. No.: WO2020/121908
PCT Pub. Date: Jun. 18, 2020

(65) Prior Publication Data
US 2022/0057311 A1 Feb. 24, 2022

(30) Foreign Application Priority Data
Dec. 13, 2018 (JP) ................. 2018-233183

(51) Int. Cl.
*G01N 3/40* (2006.01)
*G01N 33/483* (2006.01)
*G01N 33/50* (2006.01)

(52) U.S. Cl.
CPC ............ *G01N 3/40* (2013.01); *G01N 33/483* (2013.01); *G01N 33/5088* (2013.01); *G01N 2203/0076* (2013.01)

(58) Field of Classification Search
CPC ........ G01N 11/10; G01N 3/40; G01N 33/483; G01N 33/5088; G01N 2203/0076; G01N 2203/0012; G01N 2203/0676
See application file for complete search history.

(56) References Cited

U.S. PATENT DOCUMENTS

2010/0274209 A1* 10/2010 Roe .................. A61F 13/82
604/378
2017/0119742 A1 5/2017 Katsumata et al.

FOREIGN PATENT DOCUMENTS

JP 2006-329850 A 12/2006
JP 2010-227591 A 10/2010
(Continued)

OTHER PUBLICATIONS

Extended European Search Report issued in European patent application No. 19895626.0 dated Aug. 5, 2022.
(Continued)

*Primary Examiner* — Alexander A Mercado
(74) *Attorney, Agent, or Firm* — Greenblum & Bernstein, P.L.C.

(57) ABSTRACT

For providing a method capable of physically and objectively evaluating the consistency and state of a stool, provided is a method for measuring a stool consistency with a texture analyzer provided with a probe, the probe having a shape capable of measuring a consistency of a stool in a liquid form and in a solid form.

5 Claims, 3 Drawing Sheets

(56) References Cited

FOREIGN PATENT DOCUMENTS

| JP | 2018-54445 A | 4/2018 |
|---|---|---|
| WO | 2015/190568 A1 | 12/2015 |
| WO | 2017/195798 | 11/2017 |

OTHER PUBLICATIONS

Aichbichler et al. "A Comparison of Stool Characteristics from Normal and Constipated People", Digestive Diseases and Sciences, vol. 43, No. 11 (Nov. 1998), pp. 2353-2362.

Seppänen et al. "Removing lactose from milk does not delay bowel function or harden stool consistency in lactose-tolerant women", European Journal of Clinical Nutrition (2008) 62, 727-732.

Nakaji et al. "New method for the determination of fecal consistency and its optimal value in the general population", Journal of Gastroenterology and Hepatology (2002) 17, 1278-1282.

Notice of Reasons for Refusal issued May 31, 2023 in Japanese family member application No. Japanese Application No. 2020-559955 and English language translation thereof.

Kawai et al., "*Effect of Fermented Milk Containing Bifidobacterium on Bowel Habits of Healthy Volunteers with Mild Constipation*", Enterobacilli Study Magazine, 2011, vol. 25, No. 3, pp. 181-187.

O'Donnell, L. et al., "Detection of pseudodiarrhoea by simple clinical assessment of intestinal transit rate", BMJ, vol. 300, Feb. 17, 1990, pp. 439-440.

Exton-Smith, A.N. et al., "A new technique for measuring the consistency of faeces: a report on its application to the assessment of Senokotot therapy in the elderly", Age and Aging, 4, 1975, pp. 58-62.

International Search Report issued in International Patent Application No. PCT/JP2019/047360, dated Mar. 3, 2020, along with English translation thereof.

Written Opinion of the International Searching Authority issued in International Patent Application No. PCT/JP2019/047360, dated Mar. 3, 2020, along with English translation thereof.

\* cited by examiner

Fig.1(A)
Fig.1(B)
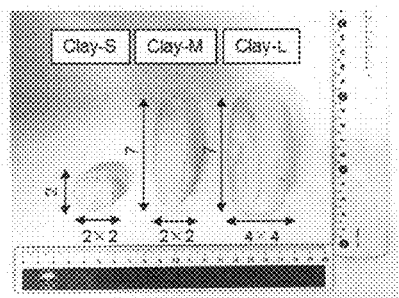
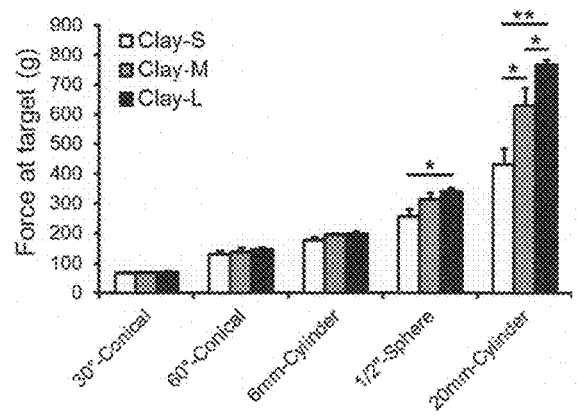
Fig.2(a) Fig.2(b) Fig.2(c) Fig.2(d) Fig.2(e)
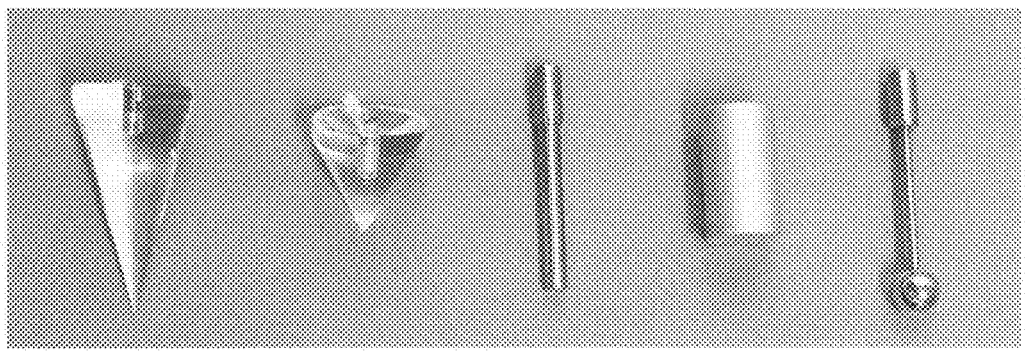
Fig.3
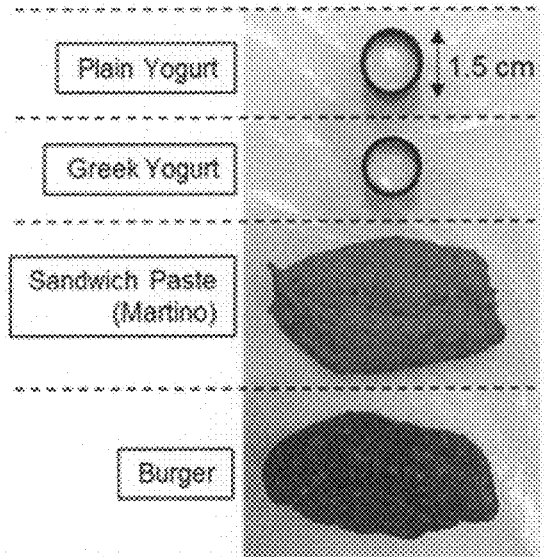

METHOD FOR MEASURING STOOL CONSISTENCY AND METHOD FOR EVALUATING STOOL STATE USING SAME

TECHNICAL FIELD

The present invention relates to a method for measuring a stool consistency and a method for evaluating a stool state using the same.

BACKGROUND ART

Evaluating the state of a stool is useful for managing the physical condition and estimating an influence of a subject substance, such as a drug.

The Bristol stool form scale (BS) score has been used as an index for evaluating a stool state (NPL 1). The BS score is however a scale for subjective determination by an evaluator which has been established as an index of the intestinal transit time, and thus it is difficult to fully eliminate the influence of the evaluator's psychology and in addition, the consistency of a stool may not necessarily match the appearance thereof.

As another index for evaluating the state of a stool, a method for evaluating the consistency of the stool with a penetrometer (an instrument for measuring the penetration depth of a probe with a certain weight freely fallen from a sample surface) is also reported (NPL 2). This method however has a problem in that a stool in an amount of 50 g or more is needed (thus, about 30% of stools are out of the range).

CITATION LIST

Non-Patent Literature

NPL 1: O'Donnell L J et al. Detection of pseudodiarrhoea by simple clinical assessment of intestinal transit rate, BMJ 300: 439-40 (1990)

NPL 2: Exton-Smith A N et al. A new technique for measuring the consistency of faeces: a report on its application to the assessment of Senokotot therapy in the elderly, Age Ageing 4: 58-62 (1975)

SUMMARY OF INVENTION

Technical Problem

Accordingly, the present invention has an object to provide a method capable of physically and objectively evaluating the consistency and state of a stool.

Solution to Problem

As a result of intensive studies for solving the above problem, the present inventors have found that the consistency and state of a stool can be physically and objectively evaluated by measuring the stool with a texture analyzer provided with a probe having a certain performance, thus completing the present invention.

Specifically, the present invention relates to a method for measuring a stool consistency with a texture analyzer provided with a probe,
the probe having a shape capable of measuring a consistency of a stool in a liquid form and in a solid form.

In addition, the present invention relates to a method for evaluating a stool state, the method including determining a state of a stool based on the natural logarithm of a force at target measured by the method for measuring a stool consistency.

Furthermore, the present invention relates to a method for evaluating an influence of a subject substance on a stool, the method including evaluating stool states before and after administration of the subject substance by the method for evaluating a stool state.

Advantageous Effects of Invention

According to the present invention, the consistency and state of a stool can be physically and objectively evaluated whatever properties the stool has.

Thus, the present invention can be used for evaluating a stool state and for evaluating an influence of a subject substance on stools.

BRIEF DESCRIPTION OF DRAWINGS

FIG. 1(A) and FIG. 1(B) show a relation between the different sample sizes and the probes in Example 1(1) where stool simulation samples (clay) were used. FIG. 1(A) shows measurement samples, and FIG. 1(B) shows the consistency of each measurement sample with each measurement probe. Values show the force at target±SD. *: $p<0.05$, **: $p<0.01$ (Student t-test)

FIG. 2(a), FIG. 2(b), FIG. 2(c), FIG. 2(d), and FIG. 2(e) show the shapes of the probes used in Example 1(1). In the drawing, FIG. 2(a) shows a 30°-conical type, FIG. 2(b) shows a 60°-conical type, FIG. 2(c) shows a 6 mm-diameter cylinder (cylindrical shape) type, FIG. 2(d) shows a 20 mm-diameter cylinder (cylindrical shape) type, and FIG. 2(e) shows a ½-inch-sphere (spherical shape) type probe shape.

FIG. 3 shows stool simulation samples used in Example 1(2).

DESCRIPTION OF EMBODIMENTS

Figure 4A:
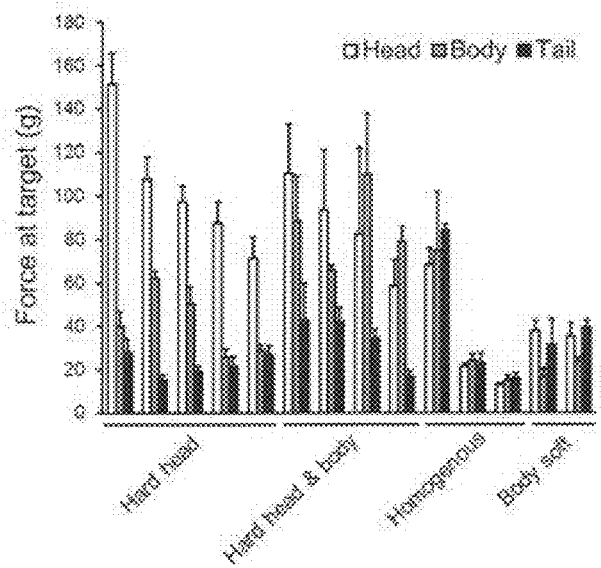
FIG. 4(A) is a graph showing the difference in the consistency among parts of each sausage-shaped dung pat (in the drawing, "Head" shows a front part, "Body" shows a middle part, and "Tail" shows a rear part).

In the method for measuring a stool consistency of the present invention, a stool consistency is measured with a texture analyzer provided with a probe. The probe has a shape capable of measuring a consistency of a stool in a liquid form and in a solid form. Here, the stool in a liquid form is, for example, a stool the viscosity of which is 3 to 7 cm/10 seconds as measured with a Bostwick viscometer, and the stool in a solid form is a stool the force at target of which can be measured with a texture analyzer in pushing a probe into the stool.

The shape of the probe is preferably a cylindrical shape or a spherical shape, for example. In addition, regarding the size of the probe, the probe has a cylindrical shape or a spherical shape with a diameter of 1 to 30 mm, preferably 5 to 15 mm. The probe is preferably a probe having a cylindrical shape with a diameter of 6 to 20 mm, preferably 6 mm, and such a probe can accurately measure the consistency even when the stool to be measured has a size as small as 2 cm square (in the case of a stool in a solid form) and has a volume as small as 5 ml (in the case of a stool in a liquid form).

The texture analyzer is not particularly limited as long as it can measure the force at target in pushing the probe into a stool. An example of the texture analyzer is TA. XT Express Enhanced Texture Analyzer manufactured by Stable Micro Systems. The conditions in measurement of the force at target are not particularly limited, and, for example, a condition where the probe is pushed into a stool at a rate of 0.01 to 20 mm/second, preferably 0.5 to 20 mm/second, and more preferably 1 to 10 mm/second to a depth of 0.5 to 20 mm, and preferably 1 to 10 mm is used. The force at target is preferably obtained by measuring a force at target multiple times while varying the measurement positions in a sample and then averaging the measured values.

In the above measurement, the stool may be a part or all of stools in a single defecation, but the stool is preferably kneaded in advance since a stool may have different consistencies from part to part. In addition, the stool is preferably made into such a thickness that the probe can be pushed therein. Furthermore, the stool may be placed in a container having a volume three times as large as the volume of the stool, as required. Note that the stool is preferably measured after brought to room temperature.

A preferred embodiment of the method for measuring a stool consistency of the present invention will be described below.

Texture analyzer: TA. XT Express Enhanced Texture Analyzer

Probe: 6 mm cylindrical shape

Measurement condition: pushing at a rate of 2 mm/second to a depth of 5 mm

Stool: kneaded in advance, for a stool in a solid form, with a size of 2 cm square or larger and 5 cm square or smaller and a weight of 10 to 100 g, preferably 10 to 30 g, for a stool in a liquid form, with a volume of 2 ml or more and 10 ml or less As described above, a stool consistency can be measured as a force at target in pushing the probe into the stool with the texture analyzer.

A stool state can be evaluated by determining the state of a stool based on the natural logarithm of a force at target measured by the method for measuring a stool consistency.

Since the force at target depends on the used probe and the measurement conditions, a criterion is required to be provided according thereto. For example, for a force at target measured in a preferred embodiment of the method for measuring a stool consistency of the present invention, the stool can be evaluated as 1 (hard) when the natural logarithm of the force at target is 4.9 or more, can be evaluated as 2 (slightly hard) when the natural logarithm is less than 4.9 and 3.6 or more, can be evaluated as 3 (normal) when the natural logarithm is less than 3.6 and 2.7 or more, can be evaluated as 4 (slightly soft) when the natural logarithm is less than 2.7 and 1.5 or more, and can be evaluated as 5 (soft) when the natural logarithm is less than 1.5.

The natural logarithm of the force at target highly correlates with the Bristol stool form scale (BS) score (NPL 1), and thus can also be allowed to correspond to the BS score.

Since the force at target depends on the used probe and the measurement conditions, a correlation with the BS score is required to be provided according thereto. For example, for a force at target measured in a preferred embodiment of the method for measuring a stool consistency of the present invention, the natural logarithm of the force at target of 4.9 or more can correspond to 1 or 2 of the BS score with a probability of 90% or more, the natural logarithm of less than 4.9 and 3.6 or more, which indicates a slightly hard stool, can correspond to 3, 4, or 5 of the BS score with a certain probability, the natural logarithm of less than 3.6 and 2.7 or more can correspond to 3, 4, or 5 of the BS score with a probability of 90% or more, the natural logarithm of less than 2.7 and 1.5 or more, which indicates a slightly soft stool, can correspond to 3, 4, or 5 of the BS score with a certain probability, and the natural logarithm of less than 1.5 can correspond to 6 or 7 of the BS score with a probability of 90% or more.

Furthermore, by evaluating stool states before and after administration of a subject substance by the method for evaluating a stool state, the influence of the subject substance on stools also can be evaluated. The subject substance is not particularly limited, and examples thereof include a food and drink containing a fermented milk, a sweetener with high sweetness degree, a dietary fiber, a vitamin, or the like, a cold medicine, a laxative, a Chinese medicine, or other substance that possibly induces a change in the stool state.

Specifically, when stool states before and after administration of a subject substance are evaluated as the same, the subject substance is determined to have no influence on stools, and when stool states before and after administration of a subject substance are evaluated as different, the subject substance is determined to have an influence on stools.

EXAMPLES

The present invention will be described in detail below with reference to examples, but the present invention is in no way limited to the examples.

Example 1

Selection of Probe:

(1) The type of the probe to be used in measurement of a stool consistency was examined by using stool simulation samples as described below as specimens. Clay, minced meat, and paste as solid samples were molded as shown in FIG. 1(A) with a spatula and were used for the consistency measurement. Greek yogurt and plain yogurt as liquid samples were placed 20 ml into a 100 ml-volume cylindrical plastic container (part No.:75.562.105 manufactured by SARSTED) and were used for the consistency measurement. First, for the purpose of selecting a measurement probe that is less affected by the difference in the sample size, consistencies of samples of the same clay having different sizes (FIG. 1(A), simulating stool consistencies of BS scores of 1 to 2) were measured with probes as described below (the shapes of the probes were shown in FIG. 2) using a texture analyzer (TA. XT Express Enhanced Texture Analyzer (Stable Micro Systems)).

<Samples>

Clay (Play-Doh, available from Hasbro)
Minced meat (Butcher's Burger LIMOUSIN, available from Delhaize)
Sandwich paste (Martino Ou Chef, available from Delhaize)
Greek yogurt (OIKOS, available from Danone)
Plain yogurt (Volle Yoghurt, available from Delhaize)

<Types of Probe> (Available from Stable Micro Systems)
30°-Conical type (FIG. 2(a))
60°-Conical type (FIG. 2(b))
6 mm-diameter Cylinder (cylindrical shape) type (FIG. 2(c))
20 mm-diameter Cylinder (cylindrical shape) type (FIG. 2(d))
½-inch Sphere (spherical shape) type (FIG. 2(e))

<Measurement Conditions of Texture Analyzer>

A probe was allowed to penetrate a flatted surface of a measurement sample at a constant rate of 2 mm/second and was pushed into a depth of 5 mm. The force at target at the time when the probe reached the point was measured. The measurement was performed five times while changing the position for each measurement sample, and the mean was taken as the consistency of the sample.

As a result of the measurement, it was apparent that as the volume of the measurement probe penetrating the sample was larger, the influence of the difference in the sample size on the measurement value was larger (FIG. 1(B)). In addition, whatever the probe is, as the sample size was smaller, the measurement value was lower. However, with the 30°-conical type, 60°-conical type, or 6 mm-diameter cylinder type which are a relatively thin measurement probe, no significant difference was detected among the measurement values on the samples of various sizes.

(2) Next, with the probes, the consistencies of stool simulation samples (FIG. 3 (minced meat, sandwich paste, Greek yogurt, plain yogurt)) were measured using the texture analyzer. In addition, for the similar samples, the viscosities were measured using a Bostwick viscometer (Bostwick Consistometer (CRI-BC 30) (CR Instruments Ltd)) which is for measurement of liquid sample viscosities. The results are shown in Table 1. Note that the samples were brought to room temperature and well kneaded before measuring the consistency or viscosity.

<Viscosity Measurement with Bostwick Viscometer>

A reservoir was filled with a measurement sample and then the gate was opened. At 10 seconds after opening, the moving distance of the sample was measured on a scale provided on the viscometer. The measurement was performed three times and the mean was taken as the viscosity of the sample.

<Measurement Conditions of Texture Analyzer>

The measurement was performed as follows. A probe was allowed to penetrate a flatted surface of a measurement sample at a constant rate of 2 mm/second and was pushed into a depth of 5 mm. The force at target at the time when the probe reached the point was measured. The measurement was performed three times for each measurement sample while changing the position, and the mean was taken as the consistency of the sample.

TABLE 1

| Sample name | Viscosity measurement value (Mean ± SD cm) | Consistency measurement value with each cylinder (Mean ± SD g) | | | | |
|---|---|---|---|---|---|---|
| | | 30° Conical | 60° Conical | 6 mm Cylinder | ½-inch Sphere | 20 mm Cylinder |
| Minced meat | n.d.* | 13.65 ± 1.21 | 28.64 ± 3.99 | 51.16 ± 2.65 | 83.70 ± 11.00 | 245.72 ± 22.80 |
| Sandwich paste | n.d.* | 4.60 ± 0.84 | 9.10 ± 0.84 | 14.21 ± 2.04 | 22.47 ± 4.54 | 68.87 ± 12.07 |
| Greek yogurt | 3.60 ± 0.10 | n.d.** | n.d.** | 1.07 ± 0.11 | 2.40 ± 0.34 | 7.65 ± 0.72 |
| Plain yogurt | 6.73 ± 0.25 | n.d.** | n.d.** | 0.71 ± 0.05 | 1.76 ± 0.10 | 4.56 ± 0.20 |

*Not measurable due to solid
**Not measurable due to no resistance detected at the measurement depth With conical type probes, the consistencies of solid samples could be measured but the consistencies of liquid samples could not be measured. With the 6 mm cylinder, 20 mm cylinder, and ½-inch sphere, the consistencies of both the liquid samples and the solid samples could be measured.

Based on the above results, the 6 mm cylinder which was considered to be capable of accurately measuring a consistency of a stool in a liquid form and in a solid form even with a small amount of the sample was selected as the probe.

Example 2

Preparation of Stool Sample

It was supposed that the results possibly varied even on stools discharged at the same time depending on the dung pat to be measured for the consistency or the part therein. In this case, previous homogenization before measurement is to be considered.

Thus, the difference in the consistency among different parts in a single dung pat was examined first. Stools used were taken from three healthy adults several times each (32 specimens in total). All stools discharged in each defecation was collected into FECOTAINER (registered trade name) (AT Medical). The consistencies of the "front part (Head)", "middle part (Body)", and "rear part (Tail)" of each of a plurality of dung pats that were discharged while maintaining a sausage shape were measured using the texture analyzer with the 6 mm cylindrical shape probe selected in Example 1 under the same conditions as in Example 1. The results are shown in FIG. 4.

Figure 4B:
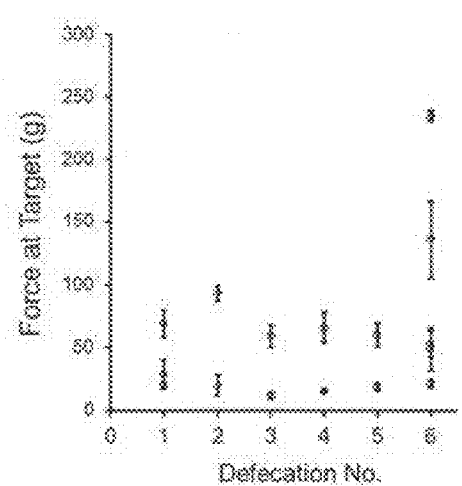
FIG. 4(B) is a graph showing the difference in the consistency among a plurality of dung pats obtained in a single defecation. Each point arranged vertically on the Defecation No. shows the consistency of each dung pat discharged in each single defecation. Values show the force at target±SD.

As a result, although there was some dung pat in which the consistencies of the respective parts were similar ("Homogenous" in FIG. 4(A)), there were many dung pats in which the consistencies from the "front part" to the "middle part" were larger (harder) than that of the "rear part" ("Hard head" and "Hard head & body" in FIG. 4(A), the difference was up to 7 times). As a rare case, there were some cases where the consistency of the "middle part" is smaller (softer) than those of the "front part" and the "rear part" ("Body soft" in FIG. 2(A)). The results show that the consistency of a dung pat can be largely different from part to part, and suggest that the measurement is required to be performed on a quite lot of parts therein for adequately evaluating the consistency of a dung pat without homogenization.

Next, with a focus on the fact that dung pats having different appearances are present together in stools obtained from a single defecation, the difference in the consistency among the dung pats was studied. As a result, even for dung pats obtained from a single defecation, the consistencies were significantly different among the dung pats (FIG. 4(B)). This result also suggests that it is difficult to evaluate the consistency of stools obtained from a single defecation without homogenization.

It was found from the above results that all dung pats obtained from a single defecation are preferably kneaded and homogenized to prepare a sample to be used in a stool consistency measurement.

Example 3

Correlation with BS Score:

The subjects were forty healthy adult men and women of 18 or higher years old. The subjects recorded on a diary the time, whether the straining in the defecation was present, and whether the residual stool feeling after the defecation was present for all defecations in a period for taking stools. At the same time, the subjects collected all the discharged stools into a stool collecting plastic container (product name: 2-Piece Specimen Collector, part No.: DYND36500, manufactured by Medline), and recorded on the diary the observation result of the stool properties. The mean±standard deviation of the stool weights was 87.25±59.46 g. For evaluating the stool properties, the BS score was used, specifically, the collected stool was compared with the BS chart provided on the diary and the score of a schematic that was considered as the most proper for describing the shape was recorded.

The stools collected in the stool collecting plastic container were temporarily stored in an airtight state at a low temperature (10° C. or lower) in a simple refrigerator in the subject's home after the subject recorded the BS score. Subsequently, the stools were quickly transported to a laboratory, and were subjected to measurement therein as described later. The series of transportations were performed in a state always maintained at a low temperature of 10° C. or lower. The same stools transported to the laboratory were observed by one researcher, who recorded the BS scores and at the same time, measured the consistencies of the stools in a manner as described later.

All the specimens in the stool collecting container were transferred into a plastic bag and were kneaded with a hand for homogenization. Apart thereof was taken with a sterilized spoon (part No.: EPY9.1, manufactured by Carl Roth) into 100 mL volume cylindrical plastic container (part No.: 75.562.105, manufactured by SARSTEDT). This was allowed to stand at room temperature for one hour to make the sample temperature close to room temperature, and then the consistency of the stool sample was measured using a texture analyzer (TA. XT Express Enhanced Texture Analyzer (manufactured by Stable Micro Systems)). As a measurement probe, a 6 mm-diameter cylinder type probe was used. The sample surface was flatted with a plastic cell spreader and the measurement probe was allowed to penetrate the sample at a constant rate of 2 mm/second and was pushed into a depth of 5 mm. The force at target (g) at the time when the probe reached the point was measured. The measurement was repeatedly performed five times at different positions for each sample and the mean of the three values except for the highest and lowest values of the five measurement values was calculated as the consistency of the sample. Since it was found by a preliminary experiment performed in advance that such values have a logarithmic distribution, the natural logarithm (ln g) of the measured value was used for a statistical analysis in this test.

Figure 5A:
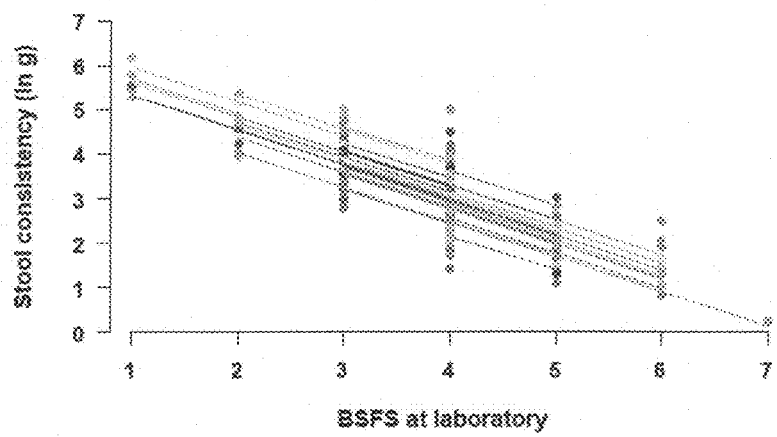
FIG. 5(A) is a graph showing the correlation between the BS scores recorded by a researcher and the natural logarithms (ln g) of the respective measured values.
Figure 5B:
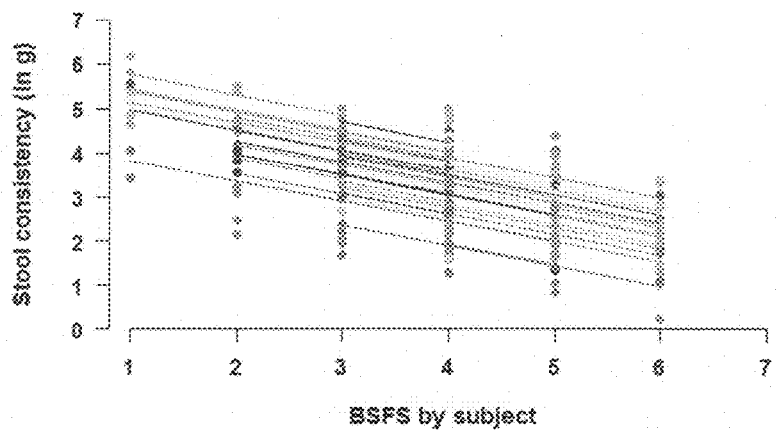
FIG. 5(B) is a graph showing the correlation between the BS scores recorded by a subject and the natural logarithms (ln g) of the respective measured values.

The results of the study on the correlation between the stool consistency measured using the texture analyzer (the natural logarithm (ln g) thereof) and the BS score are shown in FIG. 5 and Table 2.

TABLE 2

| | | Statistic | | | | |
|---|---|---|---|---|---|---|
| Variable 1 | Variable 2 | $r_{rm}$ | p | 95% CI | Intercept | Slope |
| BS researcher score | Stool consistency | −0.789 | <0.001 | [−0.835, −0.732] | 6.19 | −0.781 |
| BS subject score | Stool consistency | −0.587 | <0.001 | [−0.669, −0.491] | 5.07 | −0.459 |

It was found that the stool consistency negatively correlated with each of the BS researcher score and the BS subject score. The coefficients of correlation were both significant (P<0.001), but the researcher score had a stronger correlation with the stool consistency than the subject score. In the repeated measures correlation analysis (Bakdash J Z. et al. Repeated Measures Correlation. Frontiers in Psychology 2017; 8: 456), based on an assumption that a plurality of specimens derived from the same subject are not independent from each other, the variation in each subject is statistically adjusted by an analysis of covariance (ANCOVA). After removing the measurement variation in the subject, a parallel regression line is applied for each subject. The slope of the regression line is common among the subjects and the intercept thereof is a value specific for each subject. In the subject score, the dispersion among the regression lines for the respective subjects was larger than in the researcher score, and thus it was found that measurement errors were present among the subjects in the scoring of the BS score.

It was found from the above results that the natural logarithm (ln g) of the measured value of the stool consistency highly correlates with the scoring of the BS score by a researcher.

Example 4

Figure 6:
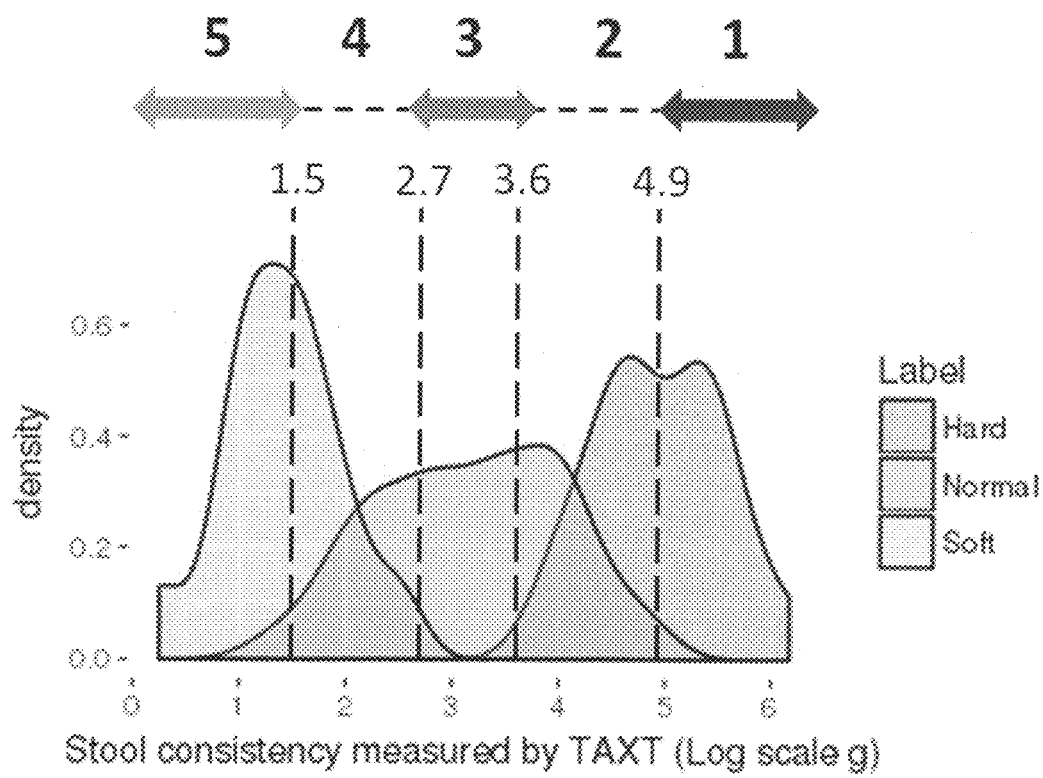
FIG. 6 is a variable graph curve of the probability density function for each category when feces specimens are divided into three shape categories based on the BS score.

The feces specimens obtained in Example 3 were divided into three shape categories: (Hard (hard stool: score 1 or 2), Normal (normal stool: score 3 to 5), and Soft (diarrhea stool: score 6 or 7)) based on the BS researcher score, and the variable graph curve of the probability density function for each category is shown in FIG. 6.

Based on FIG. 6, new criteria based on the stool consistency measurement value were set as follows.

Specifically, a stool having a log measurement value of 4.9 or more is a stool which is categorized to the BS score of 1 or 2 with a probability of 90% or more, a stool having a log measurement value of less than 4.9 and 3.6 or more is a stool which is slightly hard and is also categorized to the BS score of 3, 4, or 5 with a certain probability, a stool having a log measurement value of less than 3.6 and 2.7 or more is a stool which is categorized to the BS score of 3, 4, or 5 with a probability of 90% or more, a stool having a log measurement value of less than 2.7 and 1.5 or more is a stool which is slightly soft and is also categorized to the BS score of 3, 4, or 5 with a certain probability, and a stool having a log measurement value of less than 1.5 is a stool which is categorized to the BS score of 6 or 7 with a probability of 90% or more.

Based on the above results, a stool state can be determined in a more physical and objective and more accurate manner than the BS score by setting the following new criteria: the stool is evaluated as 1 (hard) when the natural logarithm of the force at target measured as above is 4.9 or more, is evaluated as 2 (slightly hard) when the natural logarithm is less than 4.9 and 3.6 or more, is evaluated as 3 (normal) when the natural logarithm is less than 3.6 and 2.7 or more, is evaluated as 4 (slightly soft) when the natural logarithm is less than 2.7 and 1.5 or more, and is evaluated as 5 (soft) when the natural logarithm is less than 1.5.

INDUSTRIAL APPLICABILITY

The present invention is capable of accurately evaluating the consistency and state of a stool, and thus can be used for checking the health state and for estimating an influence of a subject substance on stools.

The invention claimed is:
1. A method for evaluating a stool, comprising:
pushing a probe in the stool, the probe having a shape configured to measure the stool in at least one of a liquid form and a solid form, and
measuring the stool with a texture analyzer provided with the probe by at least determining a force at the probe as the probe is being pushed into the stool and taking a natural logarithm of the determined force,
wherein the probe has a cylindrical shape having a diameter greater than or equal to 6 mm and less than or equal to 20 mm.

2. The method for evaluating the stool according to claim 1, the method comprising measuring the force at the probe by pushing the probe at a rate of 1 to 10 mm/second into a depth of 1 to 10 mm.

3. The method for evaluating the stool according to claim 1, wherein the stool in the solid form is kneaded before the measurement.

4. The method for evaluating the stool according to claim 1, wherein the method further comprises corresponding the natural logarithm of the force at the probe to a Bristol stool form scale (BS) score, such that a natural logarithm of the force at 4.9 or more corresponds to a 1 or 2 BS score with at least a 90% probability, a natural logarithm of the force at less than 3.6 and 2.7 or more corresponds to a 3-5 BS score with at least a 90% probability, and a natural logarithm of the force at less than 1.5 corresponds to a 6 or 7 BS score with at least a 90% probability.

5. A method for evaluating a stool before and after an oral administration of a subject substance, the method comprising evaluating the stool before and after the administration of the subject substance by the method for evaluating the stool according to claim 1.

* * * * *